(12) United States Patent
Rongen et al.

(10) Patent No.: US 7,865,001 B2
(45) Date of Patent: Jan. 4, 2011

(54) SYSTEM AND METHOD FOR PREDICTING PHYSICAL PROPERTIES OF AN ANEURYSM FROM A THREE-DIMENSIONAL MODEL THEREOF

(75) Inventors: Peter Maria Johannes Rongen, Eindhoven (NL); Rudolf Theodoor Suurmond, Eindhoven (NL); Ronaldus Petrus Johannes Hermans, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 842 days.

(21) Appl. No.: 11/721,386

(22) PCT Filed: Dec. 14, 2005

(86) PCT No.: PCT/IB2005/054240

§ 371 (c)(1),
(2), (4) Date: Jun. 11, 2007

(87) PCT Pub. No.: WO2006/064479

PCT Pub. Date: Jun. 22, 2006

(65) Prior Publication Data

US 2009/0238420 A1    Sep. 24, 2009

(30) Foreign Application Priority Data

Dec. 17, 2004    (EP)    ................................. 04106664

(51) Int. Cl.
*G06K 9/00* (2006.01)
(52) U.S. Cl. .................... 382/128; 382/131; 382/154
(58) Field of Classification Search ................. 382/128, 382/131, 154; 600/411, 443
See application file for complete search history.

(56) References Cited

U.S. PATENT DOCUMENTS

| 6,463,317 | B1 * | 10/2002 | Kucharczyk et al. ........ 600/411 |
| 6,782,284 | B1 | 8/2004 | Subramanyan et al. |
| 6,905,468 | B2 * | 6/2005 | McMorrow et al. ......... 600/443 |
| 2002/0002447 | A1 | 1/2002 | Keane |
| 2003/0076987 | A1 | 4/2003 | Wilson et al. |
| 2003/0099386 | A1 | 5/2003 | Schneider et al. |

FOREIGN PATENT DOCUMENTS

| WO | 0122362 A1 | 3/2001 |
| WO | 0229758 A2 | 4/2002 |

OTHER PUBLICATIONS

Cebral Jr, et al; "Cerebral Aneurysm Hemodynamics", Biomedical Imaging: Macro to Nano, IEEE International Symposium, 2004, pp. 944-947, XP010774089.

(Continued)

*Primary Examiner*—Tom Y Lu

(57) ABSTRACT

A three-dimensional rotational angiography (3DRA) system, in which a finite element method (FEM) package is incorporated which can read in surface meshes (20b) of a reconstructed 3DRA image of an aneurysm to generate FEM meshes (20a) which are closely approximated to the observed aneurysm (20b) in an iterative process by changing the material properties of the aneurysm used in generating the simulated representations (20a) thereof. Thus, the material properties of the closely approximated simulated representation (20a) can be used in subsequent analysis of the physical properties of the aneurysm under consideration.

8 Claims, 3 Drawing Sheets

OTHER PUBLICATIONS

Cebral Jr et al; "From Medical Images", International Journal of Numerical Methods in Engineering, vol. 51, No. 8, 2001, pp. 985-1008, XP008037771.

Hector V. Ortega; "Computer Simulation Helps", Journal Articles by Fluent Software Users, JAO71, HTTP://WWW.FLUENT.COM/SOLUTIONS/ARTICLES/JA071.PDF.

Imre Bojtar, et al; Seminars on Mechanics, HTTP://WWW.ME.BME.HU/ESEMENY/SZILSZEM/KIADV03.PDF, pp. 7-8, 2003.

Humphrey J. and Canham P: "Structure, Mechanical Properties and Mechanics of Intracranial Saccular Aneurysms", J. of Elasticity, vol. 61, pp. 49-81, 2000.

Wulandana R: "A Non-Linear and Inelastic Constitutive Equation for Human Cerebral Arterial and Aneurysm Walls", PhD Thesis, University of Pittsburg, 2003.

\* cited by examiner

SYSTEM AND METHOD FOR PREDICTING PHYSICAL PROPERTIES OF AN ANEURYSM FROM A THREE-DIMENSIONAL MODEL THEREOF

This invention relates generally to a system and method for predicting physical properties of an aneurysm from a three-dimensional model thereof.

Cerebral aneurysms are pathological dilations of cerebral arteries that tend to occur near arterial bifurcations in the circle of Willis, and are usually caused by a weakening in the vessel wall. The most serious consequence, particularly if the patient has elevated blood pressure, is their rupture leading to intracranial haemorrhage and, possibly, death. The genesis, growth and rupture mechanisms are not currently well understood.

Three dimensional rotational angiography (3DRA) is a relatively new technique for imaging blood vessels in the human body. The reconstructed 3D high resolution images created from rotational digital substraction angiography data allows for potentially interesting quantitative studies. Digital substraction angiography (DSA) is the imaging standard for depiction of intracranial aneurysms and determination of their size, neck and relationship to the vascular tree. Three-dimensional rotational angiography (3DRA) produces maximum intensity projection (MIP) and shaded surface display (SSD) images giving three-dimensional visualisation of data created from the rotational DSA. These high resolution images of the cerebral aneurysm can be viewed from any desired angle and, theoretically at least, aneurysm volume can be estimated.

During (cerebral) vascular interventions, it is of prime importance to assess the dimensions and properties of aneurysms in order to select the correct treatment for the patient. Usually, however, the 3DRA reconstruction of the aneurysm only provides information about the geometry of this pathology. In order to obtain additional information, it is necessary to set up models for mechanical and material behaviour that describe the aneurysm. In "Computer Simulation Helps Predict Cerebral Aneurysms", Hector V. Ortega (http://www.fluent.com/solutions/articles/ja071.pdf), it is reported that accurately simulating the flow of blood within the aneurysm helps researchers to predict the growth pattern of the aneurysm and the danger of rupturing. It is stated therein that the behaviour of any aneurysm depends on its geometry and haemodynamics, and a computer simulation technique is proposed for studying aneurysms, taking into account its own properties such as geometry, blood flow characteristics, blood density, viscosity and velocity. However, this technique is concerned with simulation of blood flow within a given aneurysm having a given geometry and using measured physiological parameters.

It is an object of the present invention to provide a system and method for predicting physical properties, i.e. unknown physiological parameters, of an aneurysm wall so as to provide a physician with additional, patient specific, information about the pathology, to assist in treatment planning.

In accordance with the present invention, there is provided a system for analysing properties of an aneurysm, the system comprising:

imaging means for generating a three-dimensional representation of said aneurysm;

simulation means for generating a simulated aneurysm shape and approximating said simulated aneurysm shape to said three-dimensional representation of said aneurysm so as to generate a simulated representation of said aneurysm, said simulated representation having associated therewith data defining a distribution of one or more material properties in respect thereof; and means for outputting data indicative of one or more material properties of said aneurysm derived from said simulated representation thereof.

Also in accordance with the present invention, there is provided a method for analysing properties of an aneurysm, the method comprising:

generating a three-dimensional representation of said aneurysm;

generating a simulated aneurysm shape and approximating said simulated aneurysm shape to said three-dimensional representation of said aneurysm so as to generate a simulated representation of said aneurysm, said simulated representation having associated therewith data defining a distribution of one or more material properties in respect thereof; and outputting data indicative of one or more material properties of said aneurysm derived from said simulated representation thereof.

Thus, unknown physiological parameters of an aneurysm can be predicted by fitting the simulated representation (in respect of which there is a set of estimated or predicted physiological parameters) to the three-dimensional representation of the aneurysm and then assigning the physiological parameters of the resultant simulated representation to the aneurysm itself. These physiological parameters or material properties of an aneurysm may comprise geometry constants, such as wall thickness, elasticity constants of the elastin part of the blood vessel, such as Young's modulus or Poisson ratio, anisotropic data, such as collagen fibre directions and corresponding stiffness (for each layer of the blood vessel), and growth parameters, such as collagen thickening and lengthening time constants, etc. It will be appreciated by a person skilled in the art that the parameters are dependent on the specific type of material model chosen for the aneurysm wall.

Beneficially, the imaging means comprises three-dimensional rotational angiography (3DRA) means. In a preferred embodiment, the simulation means comprises a finite element method (FEM) simulation package, which beneficially employs a non-linear constitutive model describing the behaviour of an aneurysm wall. In a preferred embodiment, the simulated representation is approximated to the three-dimensional representation by iteratively comparing said simulated representation to said three-dimensional representation, using a resultant difference measure to estimate new material properties, and then repeating the simulation process to generate a new simulated representation.

The three-dimensional representation and the data indicative of one or more material properties of the respective aneurysm may be displayed simultaneously. Means may be provided to perform one or more geometrical measurements in respect of the three-dimensional representation, which geometrical measurements may be incorporated in the simulation process for generating a simulated representation.

These and other aspects of the present invention will be apparent from, and elucidated with reference to, the embodiments described herein.

Embodiments of the present invention will now be described by way of examples only and with reference to the accompanying drawings, in which.

The present invention is primarily concerned with the case where weakening of the vessel wall is the central cause of aneurysm formation. The system of the present invention is arranged and configured generally to derive physical models and performing numerical simulations, aiming to predict both mechanical and geometrical quantities involved in the formation of, for example, cerebral saccular aneurysms, which numerical simulations are based on advanced elasticity theory.

Figure 1:
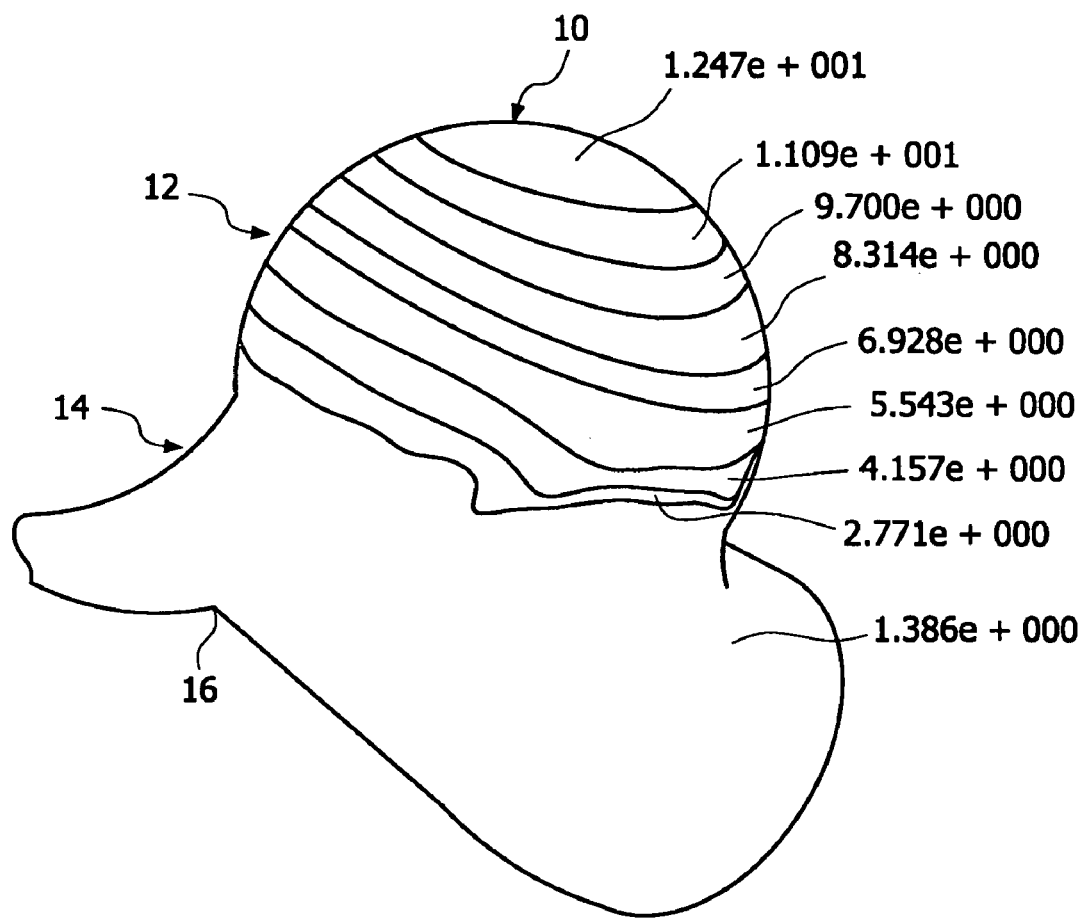
FIG. 1 illustrates an exemplary surface mesh of an aneurysm simulated by means of an FEM technique.

In the first instance, it has been determined, by performing numerical simulations of aneurysm formation using a finite element software package such as Marc/Mentat 2000, that a neck-like geometry of a saccular aneurysm can be explained by using a distribution of mechanical properties, such that the geometry is elastically weak at its centre, but substantially as stiff as the parent blood vessel near its boundary, as can be seen from FIG. 1 which depicts an example of an aneurysm simulated by means of a Finite Element Method (FEM) illustrating the total maximum strain to which the aneurysm wall is subjected at various locations. It can be seen that the maximum strain occurs at the dome 10, it then decreases steadily around the fundus 12 and is substantially as stiff at the neck 14 as the parent blood vessel 16. By applying the above-mentioned distributions of mechanical properties to simulate the deformation of a weakened curved circular area 18 of the blood vessel 16, it has been determined that a typical aneurysm shape starts to develop.

Figure 3:
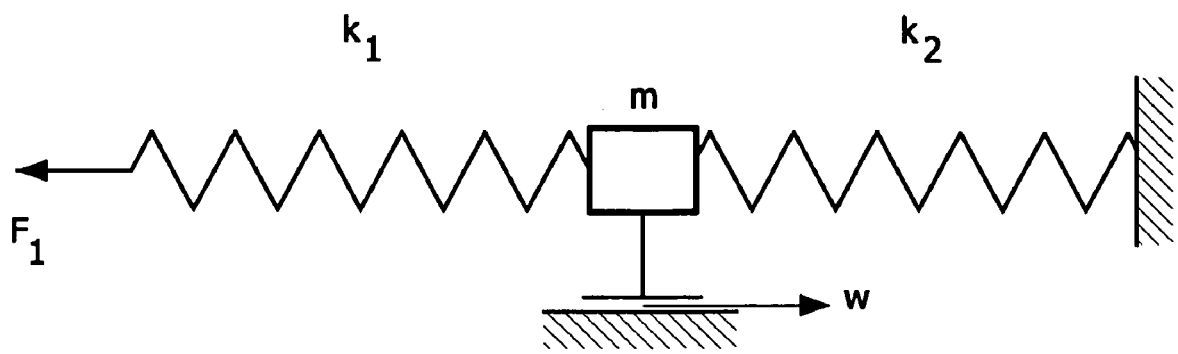
FIG. 3 is a schematic illustration of a non-linear constitutive model of an aneurysm wall.

It will be apparent to persons skilled in the art that an aneurysm wall exhibits non-linear elastic behaviour, partly due to, for example, the fact that when strains become too large, collagen activation occurs which changes the elastic properties of the anurysm wall. As a result of this non-linear behaviour, mechanical instabilities can occur during the development of an aneurysm, which mechanical instabilities may be used to predict possible rupture. Therefore, in the simulation process, it is necessary to use realistic, nonlinear constitutive models, such as the simplified model illustrated in FIG. 3 of the drawings, which incorporates collagen activation when strains become too large. FIG. 3 illustrates very simply how strain hardening (or softening) occurs when displacements and strains in the vessel wall become (very) large, and it is just an example of such behaviour. It shows that if the force in the left-hand spring becomes larger than a certain value, the other spring comes into action with a different spring constant, leading to stiffer or softer behaviour of the total structure. This, and other non-linear constitutive models of the behaviour of an aneurysm wall will be apparent to a person skilled in the art.

Figures 2A, 2B:
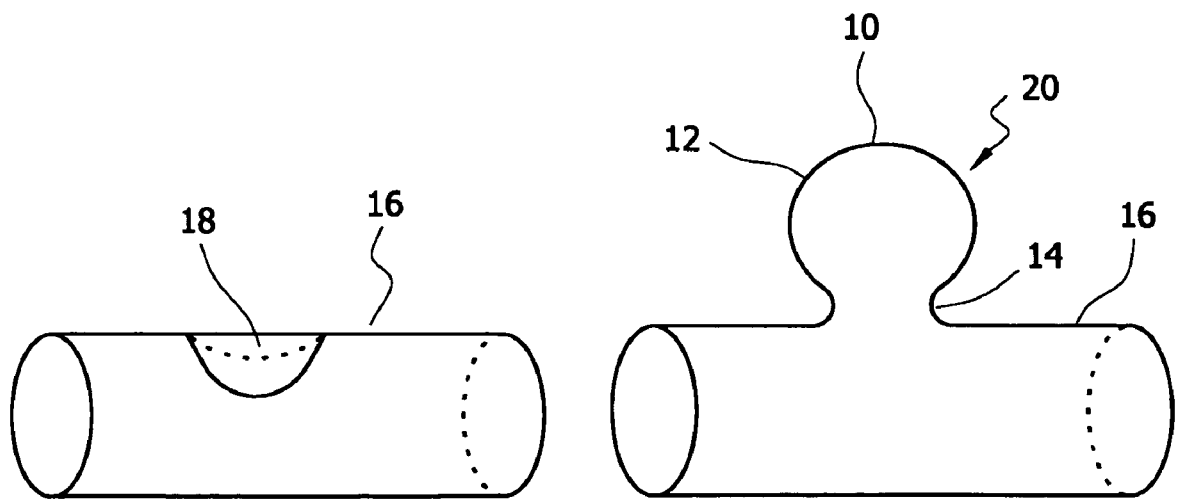
FIGS. 2a and 2b are schematic diagrams illustrating a part of a blood vessel respectively before and after the formation of an aneurysm at a weakened spot of the blood vessel wall which has been subjected to a given blood pressure.

Thus, referring to FIGS. 2a and 2b of the drawings, simulations start from an initially sound vessel wall, and can be used to simulate the growth of an aneurysm 20 when changing the vessel wall properties of a weakened spot 18 of the blood vessel wall under the influence of a given blood pressure P, such that for any given simulated aneurysm, data relating to the estimated or predicted vessel wall properties thereof will be associated therewith and, by changing these material properties within the simulation, the shape of the simulated aneurysm can be changed accordingly.

Figure 4A:
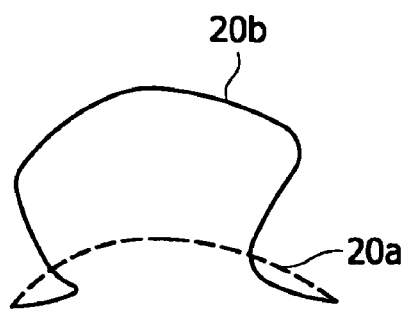
FIGS. 4a, 4b and 4c illustrate schematically the steps involved in fitting a simulated representation of an aneurysm to an observed representation of an aneurysm under consideration.
Figure 4B:
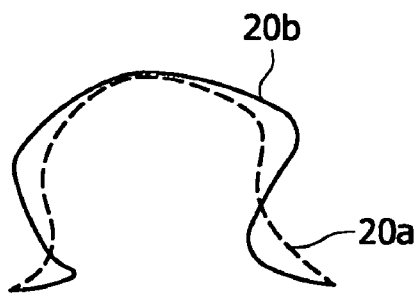
Figure 4C:
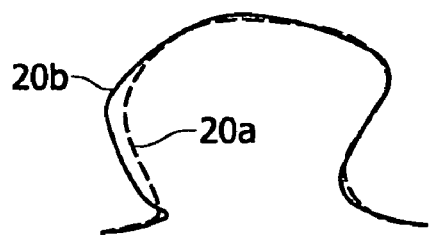

Thus, the present invention is concerned with the investigation of the so-called "inverse problem", and employs a combination of three-dimensional image data, such as three-dimensional rotational angiography (3DRA) data, with the simulation results. In general, the "inverse problem" involves fitting the simulated representation to the three-dimensional representation thereof by changing the material properties in the simulated representation to effect a required change. Referring to FIG. 4a of the drawing, therefore, the initial simulated representation 20a does not even closely resemble the 3DRA representation 20b of an aneurysm under consideration, so the material properties in the simulation are changed to give a simulated representation 20a which more closely resembles the 3DRA representation 20b, as shown in FIG. 4b. The material properties can be changed as many times as is necessary such that the simulated representation 20a approximates the 3DRA representation 20b as closely as possible, as illustrated in FIG. 4c.

Because the distribution of the material properties shapes the simulated representation in a geometry that should resemble the observed 3DRA geometry, as obtained by means of a three-dimensional rotational angiography scan, as closely as possible, this distribution of material properties can provide a patient-specific estimation of the material properties of the aneurysm under consideration, as well as a more realistic estimation of the clinically relevant mechanical and geometrical properties of the aneurysm under consideration.

Figure 5:
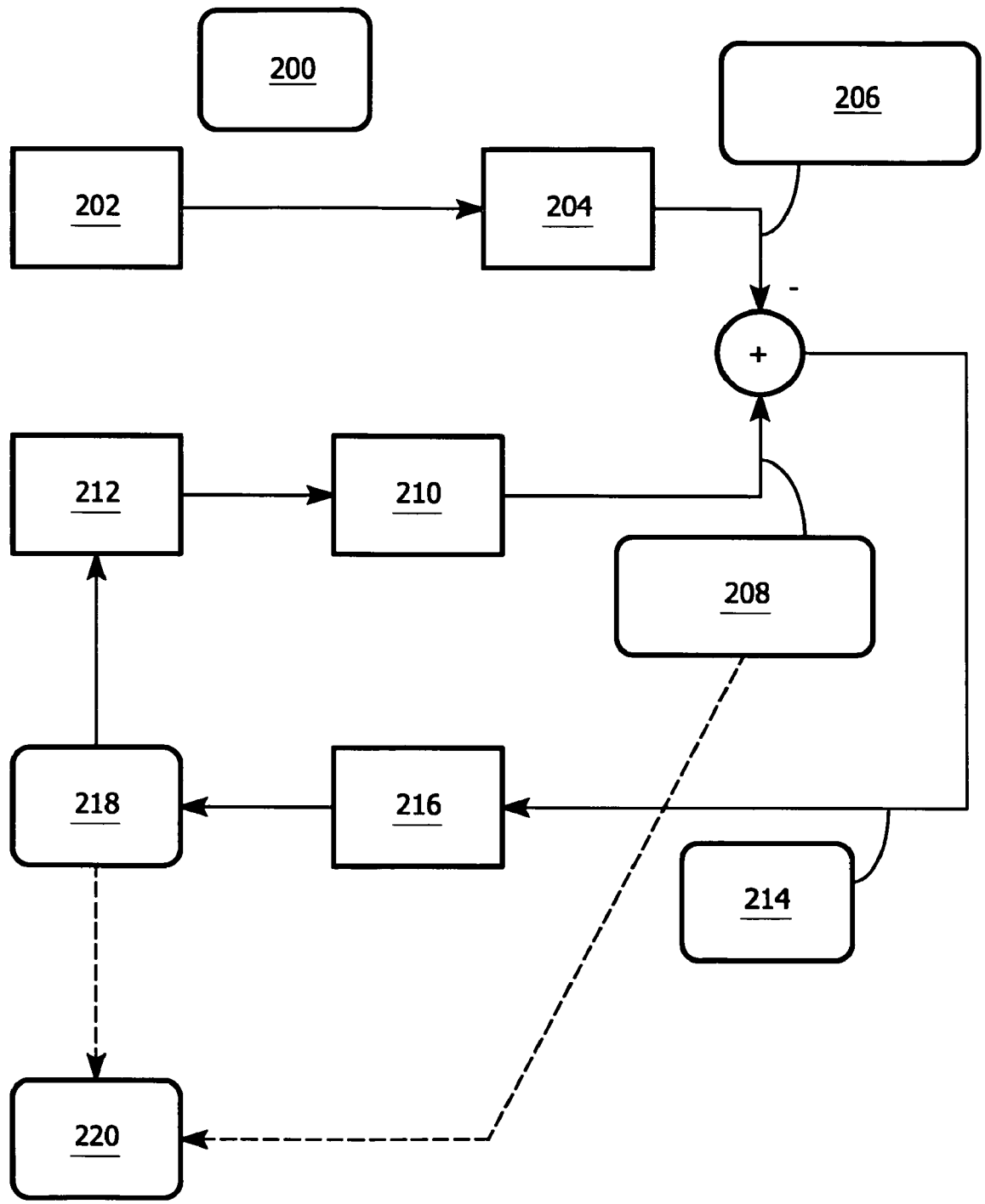
FIG. 5 is a schematic flow diagram illustrating the principle steps of a method according to an exemplary embodiment of the present invention.

Referring to FIG. 5 of the drawings, a flow diagram illustrates the principle steps of the "inverse problem" technique described above. Firstly, the angio sequence 200 is performed whereby a physician acquires a rotational angio-run at step 202 which is then sent to a 3DRA station for reconstruction, at step 204 to provide an observed aneurysm representation 206. Next, a simulated representation 208, including the associated geometry, stress and strain data, is calculated using a finite element method (FEM) simulation 210 running on the same workstation, and employing a non-linear constitutive model 212, such as that illustrated in FIG. 3 of the drawings.

The simulated representation 208 is compared with the observed representation 206 and the difference 214 is used to estimate new physical and material properties for simulation and automatically update the material parameters accordingly at step 216. This is repeated until the simulated representation is approximated closely enough to the observed representation. The outcome of the process is a physical dataset 218 of the aneurysm which can be displayed at step 220 in addition to the geometrical 3DRA data, possibly next to the normal 3DRA views. Additional information may also be provided which may support a physician in treatment planning. For example, an aneurysm severity degree may be calculated and displayed (in a similar manner to that by which a stenosis degree may be provided in respect of a coronary angiogram). Additional IVUS measurements may be acquired from the 3DRA representation and incorporated into the simulation package, for example, this may be done to include vessel and aneurysm wall thickness information in the FEM simulations. IVUS stands for Intra Vascular Ultra Sound, in which a sonic transducer is introduced into the vessel, by means of which a more detailed structure of the vessel wall and internalk features thereof can be obtained, for example, blood, thrombus, soft plaque and the different vessel layers. This information is additional to the 3DRA image, which usually shows only the lumen (in 3D).

Thus, the above-described embodiment of the present invention comprises an adaptation of a 3DRA application, in which a finite element method (FEM) package is incorporated which can read in surface meshes of a reconstructed 3DRA volume to generate FEM meshes which are closely approximated to the observed aneurysms and can be used for subsequent analysis of the physical properties of an aneurysm under consideration.

The present invention can be applied to X-ray systems equipped with a 3DRA workstation, but is also applicable to imaging systems such as MR and CT.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for analysing properties of an aneurysm (20), the system comprising:
    imaging means (202, 204) for generating a three-dimensional representation (206) of said aneurysm (20);
    simulation means (210) for generating a simulated aneurysm shape (208) and approximating said simulated aneurysm shape to said three-dimensional representation of said aneurysm so as to generate a simulated representation of said aneurysm, said simulated representation having associated therewith data defining a distribution of one or more material properties in respect thereof; and
    means (220) for outputting data indicative of one or more material properties of said aneurysm (20) derived from said simulated representation thereof.

2. A system according to claim 1, wherein said imaging means (202, 204) comprises three-dimensional rotational angiography (3DRA) means.

3. A system according to claim 1, wherein said simulation means (210) comprises a finite element method (FEM) simulation package.

4. A system according to claim 3 wherein said simulation package employs a non-linear constitutive model (212) describing the behaviour of an aneurysm wall.

5. A system according to claim 1, wherein the simulated representation is approximated to the three-dimensional representation by iteratively comparing said simulated representation to said three-dimensional representation, using a resultant difference measure to estimate new material properties, and then repeating the simulation process to generate a new simulated representation.

6. A system according to claim 1, wherein the three-dimensional representation and the data indicative of one or more material properties of the respective aneurysm (20) are displayed simultaneously.

7. A system according to claim 1, comprising means for performing one or more geometrical measurements in respect of the three-dimensional representation, which geometrical measurements can be incorporated in the simulation process for generating a simulated representation.

8. A method for analysing properties of an aneurysm (20), the method comprising:
    generating (202, 204) a three-dimensional representation (206) of said aneurysm (20);
    generating (210) a simulated aneurysm shape (208) and approximating (214, 216) said simulated aneurysm shape to said three-dimensional representation (206) of said aneurysm so as to generate a simulated representation of said aneurysm (20), said simulated representation having associated therewith data (218) defining a distribution of one or more material properties in respect thereof; and
    outputting (220) data indicative of one or more material properties of said aneurysm (20) derived from said simulated representation thereof.

* * * * *